United States Patent
Nonomura et al.

(10) Patent No.: US 7,569,534 B2
(45) Date of Patent: Aug. 4, 2009

(54) SHEET-LIKE BODY CLEANING MATERIAL

(75) Inventors: Yoshimune Nonomura, Sumida-ku (JP); Keiko Matsuo, Sumida-ku (JP); Takashi Kawai, Haga-gun (JP)

(73) Assignee: Kao Corporation, Tokyo (JP)

( * ) Notice: Subject to any disclaimer, the term of this patent is extended or adjusted under 35 U.S.C. 154(b) by 159 days.

(21) Appl. No.: 11/573,075

(22) PCT Filed: May 27, 2005

(86) PCT No.: PCT/JP2005/009776

§ 371 (c)(1),
(2), (4) Date: Feb. 26, 2007

(87) PCT Pub. No.: WO2006/013671

PCT Pub. Date: Feb. 9, 2006

(65) Prior Publication Data

US 2007/0219107 A1    Sep. 20, 2007

(30) Foreign Application Priority Data

Aug. 3, 2004  (JP) ............................. 2004-226661
Aug. 3, 2004  (JP) ............................. 2004-226662

(51) Int. Cl.
*C11D 17/04* (2006.01)
*C11D 1/94* (2006.01)
*C11D 3/43* (2006.01)

(52) U.S. Cl. ................ 510/438; 510/130; 510/159; 510/432; 510/439

(58) Field of Classification Search ............... 510/130, 510/159, 438, 439, 432
See application file for complete search history.

(56) References Cited

U.S. PATENT DOCUMENTS

| | | | | |
|---|---|---|---|---|
| 5,891,835 A * | 4/1999 | Vlasblom | .................... | 510/143 |
| 5,968,204 A * | 10/1999 | Wise | .............................. | 8/142 |
| 6,010,993 A * | 1/2000 | Romano et al. | ............. | 510/309 |
| 6,376,443 B1 * | 4/2002 | Julemont | .................... | 510/238 |
| 6,380,152 B1 * | 4/2002 | Julemont et al. | ............ | 510/438 |
| 6,410,499 B1 * | 6/2002 | Julemont et al. | ............ | 510/438 |
| 6,680,287 B2 * | 1/2004 | Wisniewski et al. | ......... | 510/438 |
| 6,703,033 B2 * | 3/2004 | Smadi et al. | ................ | 424/402 |
| 2002/0174500 A1 * | 11/2002 | Micciche et al. | ......... | 15/104.93 |
| 2004/0204332 A1 * | 10/2004 | Dastbaz et al. | .............. | 510/438 |

FOREIGN PATENT DOCUMENTS

| | | |
|---|---|---|
| JP | 11-99088 | 4/1999 |
| JP | 11-322579 | 11/1999 |
| JP | 2001 181134 | 7/2001 |
| JP | 2001-522792 | 11/2001 |
| JP | 2002-306367 | 10/2002 |
| JP | 2002 363063 | 12/2002 |
| JP | 2003 027094 | 1/2003 |
| JP | 2003 095861 | 4/2003 |
| JP | 2004 203794 | 7/2004 |
| WO | WO 99/24012 | 5/1999 |

* cited by examiner

*Primary Examiner*—Lorna M Douyon
(74) *Attorney, Agent, or Firm*—Oblon, Spivak, McClelland, Maier & Neustadt, P.C.

(57) ABSTRACT

A sheet-like body cleaning material comprising a woven fabric or nonwoven fabric sheet impregnated with an aqueous cleaning liquid containing 10 to 30% by weight of a surfactant an 10 to 25% by weight of ethanol, wherein the aqueous cleaning liquid is contained in an amount of 0.5 to 4 g based on 1 g of the sheet.

15 Claims, No Drawings

SHEET-LIKE BODY CLEANING MATERIAL

FIELD OF THE INVENTION

The present invention relates to a sheet-like body cleaning material used in a foamed state by the addition of water.

BACKGROUND ART

A cleaning sheet which is prepared by impregnating, for example, a nonwoven fabric with a surfactant which is used in a foamed state by the addition of water has been known in the art (Patent Document 1, Patent Document 2, and Patent Document 3). It is required for the sheet to have a moderate strength and soft feeling to the touch because the sheet is used to clean the skin by massaging the skin. It is also required for the cleaning liquid which contains a surfactant to be less irritant and to have a good foamability. However, there is the case where conventional cleaning sheets damage the skin when the skin is rubbed excessively while cleansing and these cleaning sheets are therefore unsatisfactory.

These cleaning sheets are preserved in the condition that these sheets are stacked on each other and packaged in a tightly sealed state. However, there is, for example, such a problem that the sheets stick together and foam up when they are taken out. Such problems concerning the appearance or convenience of products give a very unfavorable impression to consumers, which is undesirable.

Also generally an aqueous liquid containing a surfactant in a high concentration is highly viscous and it is therefore difficult to impregnate the sheet efficiently in the production process.

Patent Document 4 describes a wet fiber sheet impregnated with a cleansing composition having a pH of 3 to 6 and containing ethanol in a specified amount. However, this fiber sheet uses a combination of ethanol benzoic acid and paraoxybenzoates for mildew-proofing. This fiber sheet is used for wiping applications such as wet tissues, and thus it is not intended to be used in a foamed state.

[Patent Document 1] JP-A-2003-27094
[Patent Document 2] JP-A-2002-363063
[Patent Document 3] JP-A-2003-95861
[Patent Document 4] JP-A-11-99088

DISCLOSURE OF THE INVENTION

The present invention provides a sheet-like body cleaning material comprising a woven fabric or nonwoven fabric sheet impregnated with an aqueous cleaning liquid containing 10 to 30 by weight of a surfactant and 10 to 25% by weight of ethanol, wherein the aqueous cleaning liquid is contained in an amount of 0.5 to 4 g based on 1 g of the sheet.

The present invention relates to a sheet-like body cleaning material which has suppressed foaming when taken out of a container, and which provides a mild feeling to the skin and has a good feeling in actual use.

The inventors of the present invention have found that a sheet-like body cleaning material which has suppressed foaming when taken out of a container piece by piece, and which provides a mild feeling to the skin and has a good feeling in actual use is obtainable by impregnating a woven fabric or nonwoven fabric sheet with an aqueous cleaning liquid containing a surfactant and ethanol in specified amounts.

The sheet-like body cleaning material of the present invention is substantially free from such a phenomenon that the sheets stick together in a container and it has suppressed foaming when taken out of a container piece by piece; and it has an excellent antiseptic effect and it provides a mild feeling to the skin and has a good feeling in actual use. Also, because the aqueous cleaning liquid has a low viscosity it has good impregnation ability in the production of the sheet.

The surfactant to be used in the present invention may be any of an anionic surfactant, nonionic surfactant, and amphoteric surfactant having a foaming property suitable to be used as the body cleaning material.

Examples of the anionic surfactant include polyoxyalkylene alkyl ether sulfates, alkyl sulfates, alkyl ether carboxylates, fatty acid amide ether carboxylates, higher fatty acid salts, alkyl phosphates, N-acyl amino acids, acylated isethionate, acylated taurate, N-alkylamidealkanol sulfate, and polyoxyalkylene fatty acid amide ether sulfate.

The alkyl groups or acyl groups of these anionic surfactants are preferably those having a straight-chain containing 10 to 14 carbon atoms, which may have a methyl-branched alkyl group partly. Also, a part or all of the alkyl groups may be alkenyl groups. As the counter ion, alkali metals such as sodium and potassium are preferable.

Among these anionic surfactants, preferable examples are alkyl phosphates containing an alkyl monophosphate represented by the formula (1) and an alkyl diphosphate represented by the formula (2) in the following ratio of alkyl monophosphate:alkyl diphosphate=60:40 to 100:0.

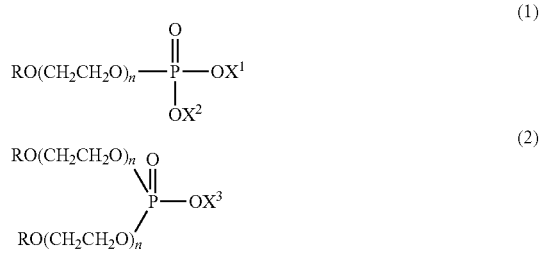

Wherein, R represents an alkyl group having an average carbon number of 9 to 15 $X^1$, $X^2$ an $X^3$ respectively represent a hydrogen atop or an alkali metal and n denotes a number of 0 to 5, which represents the average addition molar number of ethylene oxides.

Examples of the nonionic surfactant include polyoxyalkylene alkyl ethers, polyoxyalkyene fatty acid esters, alkylamine oxides, alkyl saccharides, sucrose fatty acid esters, glycerin fatty acid esters, sorbitan fatty acid esters, polyoxyalkylene glycerin fatty acid esters, polyoxyalkylene sorbitan fatty acid esters, fatty acid alkanol amides, and polyoxyalkylene hydrogenated castor oils. The alkyl groups or acyl groups of these nonionic surfactants are preferably those having a straight-chain containing 10 to 14 carbon atoms and may have a methyl-branched alkyl group partly.

Examples of the amphoteric surfactant include alkyldimethylcarbobetaine, alkyldimethylsulfobetaine, imidazoliniumbetaine, and fatty acid amidobetaine. The alkyl groups or acyl groups of these amphoteric surfactants are preferably those having a straight-chain containing 10 to 14 carbon atoms and may have a methyl-branched alkyl group partly.

The aqueous cleaning liquid so be used in the present invention preferably contains an anionic surfactant and an amphoteric surfactant from the viewpoint of foaming properties. The value of ratio by weight of the anionic surfactant/amphoteric surfactant is preferably 1 to 10 and more preferably 2 to 5.

The surfactant is contained in an amount of 10 to 30% by weight and preferably 15 to 30% by weight in the entice composition of the aqueous cleaning liquid. When the amount of the surfactants is less than 10% by weight, only insufficient foaming can be obtained whereas when the amount exceeds 30% by weight, there is the case where the feeling in actual use is deteriorated or difficulty is brought about in the preparation process.

The aqueous cleaning liquid contains 10 to 25% by weight and preferably 15 to 25% by weight of ethanol. When the amount is less than 10% by weight only insufficient viscosity-lowering effect and antiseptic effect are obtained. When the amount of ethanol exceeds 25% by weight, the foaming of the aqueous cleaning liquid is deteriorated when used.

Generally, the surfactant forms an aggregate with a higher-order structure in a high concentration to thereby thicken the cleaning liquid. This is the reason of difficult handling in the production process and of foaming during storage. It is assumed that these problems are solved by the addition of ethanol because the formation of the aggregate of the surfactant is limited.

The aqueous cleaning liquid to be used in the present invention may further contain a booster other than the surfactants. It is very important that the foaming body cleaning material secures a high foaming property. Generally, when ethanol is added, the foaming property is deteriorated. In the present invention, however, a higher foaming property can be attained by adding a booster other than the surfactants.

As the booster a fatty acid, higher alcohol, alkylglyceryl ether or the like may be used.

As the fatty acid, those having 10 to 18 carbon atoms are preferable and examples include lauric acid, myristic acid, palmitic acid, stearic acid, and isostearic acid.

As the higher alcohol, those having 10 to 18 carbon atoms are preferable and examples include lauryl alcohol, cetyl alcohol myristyl alcohol, stearyl alcohol, and isostearyl alcohol.

Examples of the alkyl glyceryl ether include those having 4 to 12 carbon atoms containing a straight-chain or branched alkyl group or alkenyl group. For example, those containing an alkyl group having 4 to 12 carbon atoms such as n-butyl group, isobutyl group, tert-butyl group, n-pentyl group, isopentyl group, n-hexyl group, isohexyl group, n-heptyl group, n-octyl group, 2-ethylhexyl group n-nonyl group n-decyl group, and n-dodecyl group are preferable.

One or more of these boosters maybe used and are contained in amount of 1 to 10% by weight and preferably 2 so 5% by weight in the entire composition of the aqueous cleaning liquid from the viewpoint of practical foaming and also from the viewpoint of keeping product qualities during long-term preservation.

The aqueous cleaning liquid to be used in the present invention may further contain a skin care agent. Examples of the skin care agent include humectants such as a polyhydric alcohol, sodium lactate, sorbitol and sodium hyaluronate; oil and fats/waxes derived from animal or vegetable oils; hydrocarbons such as liquid paraffin and vaseline sterols such as cholesterol and phytosterol; and fatty acid esters.

The skin care agents may be used alone or in combinations a dare contained an amount of 1 to 20% by weight and preferably 5 to 17% by weight in the entire composition from the viewpoint of improving the feeling in actual use.

The aqueous cleaning liquid may be formulated with, besides the above components, a disinfectant such as trichrosane and trichlorocarbanilide; anti-inflammatory agents such as a glycyrrhizic acid sale of potassium and tocopherol acetate; antiseptics such as methylparabene, ethylparabene, propylparabene, butylparabene, sodium benzoate and isopropylmethylphenol; chelating agents such as ethylenediamine tetraacetic acid or its salt and hydroxyethanediphophonic acid or its salt; and others including perfumes, cooling agents such as 1-menthol, dyes, ultraviolet absorbers, antioxidants, and vegetable extracts.

The content of water in the aqueous cleaning liquid, which essentially contains a surfactant and which may contain various components, is preferably 30 to 70 by weight.

The aqueous cleaning liquid used in the present invention has a pH of, preferably, 3 to 12 and more preferably 5 to 10 when diluted 20 times with water from the viewpoint of foaming and low irritation to the skin in practical use.

The pH may be adjusted using an aqueous solution of acid or alkali.

The pH is measured at 25° C. by a pH meter using a diluted liquid obtained by diluting the aqueous cleaning liquid 20 times with water.

The woven fabric or nonwoven fabric to be used in the present invention serves as a substrate impregnated with the above aqueous cleaning liquid. Examples of the woven fabric or nonwoven fabric include nonwoven fabrics, nit fabrics or woven fabrics made of hydrophilic fibers and/or hydrophobic fibers Examples of he hydrophilic fibers include cellulose fibers, pulp, rayon, and acryl. Examples of the hydrophobic (synthetic) fibers include a polyethylene, polypropylene, polyester polyamide, polystyrene, nylon, and acetate.

As the above woven fabric or nonwoven fabric, nonwoven fabrics made of mixed fibers of ultrafine synthetic fibers and hydrophilic fibers are preferable. As the ultrafine synthetic fibers, ultrafine fibers or split fibers made of fibers of for example, a polyethylene, polypropylene, polyester, polyamide, polystyrene, nylon or acetate are preferable. The fineness of the ultrafine synthetic fiber is preferably 0.1 to 3.3 dtex and more preferably 0.1 to 1.1 dtex. Here, the above term dtex is the weight per unit length (10000 m) of a fiber. The lower the dtex is, the finer the fiber is.

When the fiber is represented by a fiber diameter, preferred one is 10 μm or less because it provides a good feeling to the touch and air is entangled in the fiber, leading to increased foaming.

In the case of the split fibers, those having the characteristics that the fineness of 1.1 to 4.4 dtex before they are split and the number of splits is 4 to 22 are preferable in view of a narrow distance between fibers and good foaming.

Examples of the hydrophilic fibers include cellulose fibers (for examples, cotton, pulp, rayon, Cupra, Tencel fiber Lyocell) and acrylic fibers. Among these fibers, rayon is preferable.

The fiber length of the fiber is, though not particularly limits to, preferably 5 to 60 mm in view of an increase in density and good foaming properties.

The shape of the fiber is not limited, and may be a triangular form or a star form so long as no influence is exerted on the feeling to the touch.

The mixing ratio of the ultrafine synthetic fiber to the hydrophilic fiber is preferably as follows: ultrafine synthetic fiber:hydrophilic fiber=20:80 (wt) to 80:20 (wt/wt) more preferably 40:60 (wt/wt) to 60:40 (wt/wt) in view of the compatibility between the durability of the sheet and the feeling to the skin.

The basis weight of the nonwoven fabric is preferably 30 to 100 g/m$^2$ and more preferably 40 to 60 g/m$^2$.

There is no limitation to the shape and size of the sheet and an appropriate sheet may be selected from sheets having a circular square or rectangular shape depending on the purpose.

The thickness of the sheet is preferably 0.1 to 4 mm and more preferably 0.2 to 3 mm in view of convenience in handling and portability. The thickness is measured under a load of 3.7 g/cm².

The density (apparent density) is preferably 0.01 to 0.3 g/cm³, and more preferably 0.1 to 0.25 g/cm³ from the viewpoint of aqueous liquid impregnating ability and foaming when water is added during use.

It is preferably that plenty of air is entangled in the body cleaning material of the present invention when it is used in a foamed state by adding water, to improve foaming and cleansability. For this purpose the woven fabric on nonwoven fabric has a void fraction of preferably 70 to 99% and more preferably 85 to 99%; the void fraction is given by the following equation.

Void fraction (%)=(1−(ρ'ρ))×100 wherein, ρ=specific gravity of the sheet and ρ'=apparent density of the sheet.

In the body cleaning material of the present invention, the distance between fibers of the nonwoven fabric is preferably 1 to 100 μm and more preferably 1 to 50 μm to obtain excellent liquid impregnation ability and to form finer foams.

The distance of fibers is calculated in the following method. When the thickness of the nonwoven fabric is L (cm), the basis weight of the nonwoven fabric is w/(g/m²), the fineness of the fiber component i is Di (dtex), the proportion by weight of the fiber component i is αi (%), and the average diameter of the fiber component is Fd (μm), the average distance Dp between fibers is given by the following equation.

$$\text{Average distance } Dp \text{ between fibers} = \text{Average distance between fiber centers } \Delta - \text{Average diameter } Fd = 10000 \times \left( L/w \sum_{i=1}^{p} \alpha i/Di \right)^{0.5} - Fd \quad \text{[Equation 1]}$$

With regard to the fitness Di, each type of individual fibers is specified by a differential scanning calorimeter to give the density of the specified fiber. Then the fineness Di is calculated from the density di (g/cm³) and the diameter Fdi (μm) of the fiber component i according to the following equation.

$$Di = 1000000 \text{ (cm)} \times \text{Sectional area } (cm^2) \times \text{Specific gravity } (g/cm^3) = 1000000 \times \pi (Fdi/2)^2 \times di$$

The nonwoven fabric is not limited to a single layer but may be a multilayer In the case where the nonwoven fabric is a multilayer for example a three-layer, is preferable when the nonwoven fabric is designed so as to force air out of the nonwoven fabric by using a latent crimped fiber or the like to form a cushion layer as an intermediate layer, since foaming is more promoted.

Though no particular limitation is imposed on a method of producing the nonwoven fabric, a span race method or others like a wet span bond method, thermal bond method, air-through method, and resin bond method are preferable in terms of the feeling to the touch.

Also, the nonwoven fabric may be made to have a high-density part and a low-density part by giving density gradient of the fibers or by carrying out patterning by an embossing process.

In the present invention, such a base material is impregnated with the above aqueous cleaning liquid. The impregnation ratio is 0.5 to 4 g preferably 1 to 3 g and more preferably 2 to 2.5 g based on 1 g of the sheet.

The sheet-like body cleaning material impregnated with the aqueous cleaning liquid is applied as a wet type cleaning material, and preferably stored in a tightly sealed package condition.

The sheet-like body cleaning material of the present invention is preferable for cleaning the body and more preferable as a facial wash.

The sheet-like body cleaning material of the present invention can be used by adding water for foaming up upon application; it can be used for cleaning the body by massaging When the cleaning material is used as, for example, a facial wash, it is preferably used in the following method.

First a piece of sheet is taken out, spread and crumpled lightly to foam thoroughly by adding water little by little. Next, the foamed sheet is lightly folded in four to wash the whole face in such a gentle manner as to massage and then he foam is rinsed away sufficiently. At this time, is preferable to avoid such an excessively force washing operation as to cause irritation to the skin.

EXAMPLES

Examples and Comparative Examples

A sheet-like body cleaning material (content of an aqueous cleaning liquid 2.3 g/g (sheet)) having the composition shown in Table 1 was manufactured and evaluated for its foaming property upon use, feeling to the skin, foaming at the taking out action, and viscosity. The results are shown collectively in Table 1.

(Method of Evaluation)

(1) Foaming Properties Upon Use, Feeling to the Skin, and Foaming at the Taking Out:

Expert panelists added a proper amount of water to each sheet-like body cleaning material to generate foams. Each panelist washed the face by using the foamed cleaning material and rinsed the face with tap water. The foaming properties, feeling to the skin and foaming when the cleaning material was taken out were sensorially evaluated and rated according to the following standards.

(Foaming Property and Feeling to the Skin)
A: Very good
B: Good
C: Normal
D: Inferior (Foaming when the Cleaning Material is Taken Out)
A. Unobserved
B: Almost unobserved
C: Observed
D: A lot (2) Viscosity:

The viscosity was measured at 25° C. by using a BM/BL type viscometer manufactured b TOKIMEC INC. No. 2 rotor was used and the rotation speed was set to 60 rpm.

TABLE 1

|  |  | Example | | | Comparative Example | | | |
| --- | --- | --- | --- | --- | --- | --- | --- | --- |
|  |  | 1 | 2 | 3 | 1 | 2 | 3 | 4 |
| Aqueous liquid (%) | Polyoxyethylene (2) alkyl (12.13) ether phosphoric acid | 15.0 | 15.0 | 15.0 | 5.0 | 30.0 | 15.0 | 15.0 |
|  | Laurylhydroxysulfobetaine | 5.0 | 5.0 | 5.0 | 1.7 | 10.0 | 5.0 | 5.0 |
|  | Lauric acid | 1.0 | 1.0 | 1.0 | 1.0 | 1.0 | 1.0 | 1.0 |
|  | Myristic acid | 1.0 | 1.0 | 1.0 | 1.0 | 1.0 | 1.0 | 1.0 |
|  | Glycerin mono-2-ethyl hexyl ether | 2.0 | 2.0 | 2.0 | 2.0 | 2.0 | 2.0 | 2.0 |
|  | Glycerin | 15.0 | — | 20.0 | 15.0 | 15.0 | 15.0 | 15.0 |
|  | Butylene glycol | 6.0 | 6.0 | 6.0 | 6.0 | 6.0 | 6.0 | 6.0 |
|  | Sodium benzoate | 0.3 | 0.3 | 0.3 | 0.3 | 0.3 | 0.3 | 0.3 |
|  | pH adjusting agent | Proper amount | Proper amount | Proper amount | Proper amount | Proper amount | Proper amount | Proper amount |
|  | Perfume | 0.2 | 0.2 | 0.2 | 0.2 | 0.2 | 0.2 | 0.2 |
|  | Ion exchange water | 34.5 | 49.5 | 29.5 | 47.8 | 14.5 | 49.5 | 24.5 |
|  | Ethanol | 20.0 | 20.0 | 20.0 | 20.0 | 20.0 | 5.0 | 30.0 |
|  | pH of the aqueous solution diluted 20 times (25° C.) | 7 | 7 | 7 | 7 | 7 | 7 | 7 |
| Nonwoven fabric | Ultrafine synthetic fiber: polyethylene/polypropylene split fiber (fineness: 0.14 dtex) (%) | 50 | 50 | 50 | 50 | 50 | 50 | 50 |
|  | Hydrophilic fiber: Rayon (fineness: 1.7 dtex) (%) | 50 | 50 | 50 | 50 | 50 | 50 | 50 |
|  | Void fraction (%) | 90.9 | 90.9 | 90.9 | 90.9 | 90.9 | 90.9 | 90.9 |
|  | Average distance between fibers (μm) | 4.9 | 4.9 | 4.9 | 4.9 | 4.9 | 4.9 | 4.9 |
|  | Basis weight (g/m$^2$) | 55 | 55 | 55 | 55 | 55 | 55 | 55 |
| Foaming ability in actual use | | A | A | A | D | C | A | C |
| Feeling to the skin in actual use | | A | B | B | D | C | B | D |
| Foaming when the cleaning material is taken out | | A | A | A | A | C | D | A |
| Viscosity (mPa · s) | | 23 | 18 | 35 | 13 | 35 | 84 | 20 |

The invention claimed is:

1. A sheet-like body cleaning material comprising a woven fabric or nonwoven fabric sheet impregnated with an aqueous cleaning liquid comprising (A) 10 to 30% by weight of an anionic surfactant and an amphoteric surfactant, and (B) 10 to 25% by weight of ethanol, wherein the aqueous cleaning liquid comprises the anionic surfactant and the amphoteric surfactant in a ratio by weight of anionic surfactant/amphoteric surfactant of 3 to 10, wherein the anionic surfactant is at least one alkyl phosphate salt and wherein the aqueous cleaning liquid is contained in an amount of 0.5 to 4 g based on 1 g of the sheet.

2. The sheet-like body cleaning material according to claim 1, wherein a booster other than the anionic surfactant and the amphoteric surfactant is contained in an amount of 1 to 10% by weight of the aqueous cleaning liquid.

3. The sheet-like body cleaning material according to claim 1, wherein the woven fabric or nonwoven fabric is a nonwoven fabric made of a mixed fiber of a ultrafine synthetic fiber and a hydrophilic fiber.

4. The sheet-like body cleaning material according to claim 3, wherein the hydrophilic fiber is a cellulose fiber.

5. The sheet-like body cleaning material according to claim 1, wherein the aqueous cleaning liquid comprises the anionic surfactant and the amphoteric surfactant in a ratio by weight of anionic surfactant/amphoteric surfactant of 3 to 5.

6. The sheet-like body cleaning material according to claim 1, wherein the aqueous cleaning liquid comprises 15 to 25% by weight of ethanol.

7. The sheet-like body cleaning material according to claim 2, wherein the booster is contained in an amount of 2 to 5% by weight of the aqueous cleaning liquid.

8. The sheet-like body cleaning material according to claim 2, wherein the booster comprises a fatty acid, a higher alcohol, or an alkylglyceryl ether.

9. The sheet-like body cleaning material according to claim 1, wherein the aqueous cleaning liquid contains water in an amount of 30 to 70% by weight.

10. The sheet-like body cleaning material according to claim 1, wherein the aqueous cleaning liquid has a pH of 3 to 12 when diluted 20 times with water.

11. The sheet-like body cleaning material according to claim 10, wherein the pH is 5 to 10.

12. The sheet-like body cleaning material according to claim 1, wherein the amphoteric surfactant is a betaine.

13. The sheet-like body cleaning material according to claim 12, wherein the betaine is an alkylhydroxysulfobetaine wherein the alkyl has 10 to 14 carbon atoms.

14. A sealed container comprising a plurality of sheet-like body cleaning materials according to claim 1 contained therein.

15. A method of treating the skin comprising applying the sheet-like body cleaning material according to claim 1 to the skin.

* * * * *